United States Patent
Sato (10) Patent No.: US 10,031,115 B2
(45) Date of Patent: Jul. 24, 2018

(54) SYSTEM FOR MEASURING CARBON COMPONENT CONTAINED IN PARTICULATE MATTER

(71) Applicant: Ayako Sato, Shizuoka (JP)

(72) Inventor: Ayako Sato, Shizuoka (JP)

(*) Notice: Subject to any disclaimer, the term of this patent is extended or adjusted under 35 U.S.C. 154(b) by 0 days.

(21) Appl. No.: 14/781,682

(22) PCT Filed: Apr. 10, 2013

(86) PCT No.: PCT/JP2013/060801
§ 371 (c)(1),
(2) Date: Oct. 1, 2015

(87) PCT Pub. No.: WO2014/162614
PCT Pub. Date: Oct. 9, 2014

(65) Prior Publication Data
US 2016/0047783 A1    Feb. 18, 2016

(30) Foreign Application Priority Data
Apr. 4, 2013  (JP) ................. 2013-078269

(51) Int. Cl.
*G01N 31/12* (2006.01)
*G01N 31/00* (2006.01)

(52) U.S. Cl.
CPC ........... *G01N 31/12* (2013.01); *G01N 31/005* (2013.01)

(58) Field of Classification Search
CPC ..... G01N 31/12; G01N 31/005; G01N 31/007

USPC ............. 422/50, 51, 62–68.1, 82.01, 94, 98
See application file for complete search history.

(56) References Cited

FOREIGN PATENT DOCUMENTS

| JP | 2005-9964 | 1/2005 |
| JP | 2010-216977 | 9/2010 |
| JP | 2011-164020 | 8/2011 |
| JP | 2012-163545 | 8/2012 |

OTHER PUBLICATIONS

Machine English Translation-JP2011164020A, No date.*
International Search Report dated Jul. 16, 2013 in International Application No. PCT/JP2013/060801.
(Continued)

*Primary Examiner* — Samuel P Siefke
(74) *Attorney, Agent, or Firm* — Wenderoth, Lind & Ponack, L.L.P.

(57) ABSTRACT

In this system, the carbon component of atmospheric particulate matter (PM2.5) is measured by: heating a sample in a first oven under such conditions as to fractionate the carbon component into carbon fractions; completely converting each carbon fraction into carbon dioxide gas in a second oven; and then measuring the amount of carbon dioxide gas in the carbon fraction precisely. In the system, the problem that a TCD detector cannot measure a low-concentration fraction is solved by using a combustion gas in a non-diluted state, though a combustion gas diluted 150-fold is used in a conventional elemental analyzer. Thus, the present invention develops an international standard instrument in which one standard sample is used and which enables simple standardized measuring acceptable to The International System of Units (SI).

3 Claims, 8 Drawing Sheets

(56) References Cited

OTHER PUBLICATIONS

Real face of the CHN coder Hozumi Keiichiro supervision Yanaco Analytical Industry Co., Ltd. Technology Group Edit 1993 (with English translation).
Fine particulate matter in the air (PM2.5) component measurement manual Apr. 19, 2012 Ministry of Environment (with English translation).

* cited by examiner

Informal Social Gathering for Organic Microanalysis Res.
Organic Element Analysis Standard Sample cerificated
by Standard Sample Committee
SP-1 made by Kishida Chemical, Acetanilide C:71.09%

| sample amount $\mu g$ | C content % | C error dev.% | C content $\mu g$ |
|---|---|---|---|
| 3332.2 | 71.47 | 0.38 | 2381.6 |
| 3202.5 | 71.43 | 0.34 | 2287.5 |
| 1983.9 | 71.02 | -0.07 | 1409.0 |
| 2372.6 | 71.19 | 0.10 | 1689.0 |
| 2124.1 | 71.13 | 0.04 | 1510.8 |
| 1568.3 | 71.00 | -0.09 | 1113.5 |
| 1596.5 | 70.97 | -0.12 | 1133.1 |
| 1584.1 | 71.02 | -0.07 | 1125.0 |
| 1576.5 | 71.09 | 0.00 | 1120.7 |
| 1128.6 | 70.90 | -0.19 | 800.1 |
| 1231.2 | 70.87 | -0.22 | 872.6 |
| 1221.5 | 70.96 | -0.13 | 866.8 |
| 568.4 | 71.10 | 0.01 | 404.1 |
| 590.7 | 71.10 | 0.01 | 420.0 |
| 588.9 | 71.10 | 0.01 | 418.7 |

FIG. 3b

Informal Social Gathering for Organic Microanalysis Res.
Organic Element Analysis Standard Sample cerificated
by Standard Sample Committee
SP-15 made by Kishida Chemical, Iodoform C:3.05%

| sample amount $\mu g$ | C content % | C error dev.% | C content $\mu g$ |
|---|---|---|---|
| 3126.2 | 3.07 | 0.02 | 95.8 |
| 2373.8 | 3.02 | −0.03 | 71.7 |
| 1202 | 2.96 | −0.09 | 35.6 |
| 904.7 | 2.97 | −0.08 | 26.8 |
| 720.8 | 2.96 | −0.09 | 21.3 |
| 555.8 | 3.23 | 0.18 | 17.9 |
| 364.1 | 3.22 | 0.17 | 11.7 |
| 171.7 | 3.10 | 0.05 | 5.3 |

FIG. 4

Informal Social Gathering for Organic Microanalysis Res.
Organic Element Analysis Standard Sample cerificated
by Standard Sample Committee
SP-9 made by Kishida Chemical, Antipyrin C:70.19% H: 6.43% N: 14.88%

| sample amount | C thoeretrical value | C measured value | error | H thoeretrical value | H measured value | error | N thoeretrical value | N measured value | error |
|---|---|---|---|---|---|---|---|---|---|
| μg | μg | μg | μg | μg | μg | μg | μg | μg | μg |
| 333.8 | 234.3 | 235.2 | 0.9 | 21.5 | 21.7 | 0.2 | 49.7 | 49.2 | -0.5 |
| 316.6 | 222.2 | 222.6 | 0.4 | 20.4 | 21.7 | 1.3 | 47.1 | 49.9 | 2.8 |
| 315.8 | 221.7 | 221.6 | -0.1 | 20.3 | 20.5 | 0.2 | 47.0 | 47.0 | 0.0 |
| 377.0 | 264.6 | 264.1 | -0.5 | 24.2 | 24.0 | -0.2 | 56.1 | 56.2 | 0.1 |
| 362.2 | 254.2 | 253.9 | -0.3 | 23.3 | 22.7 | -0.6 | 53.9 | 54.0 | 0.1 |
| 362.5 | 254.4 | 255.0 | 0.6 | 23.3 | 23.4 | 0.1 | 53.9 | 53.6 | -0.3 |
| 361.3 | 253.6 | 253.3 | -0.3 | 23.2 | 22.5 | -0.7 | 53.8 | 53.8 | 0.0 |
| 306.2 | 214.9 | 214.0 | -0.9 | 19.7 | 19.4 | -0.3 | 45.6 | 45.9 | 0.3 |

SYSTEM FOR MEASURING CARBON COMPONENT CONTAINED IN PARTICULATE MATTER

TECHNICAL FIELD

The present invention relates to measuring carbon component contained in atmospheric particulate matter.

BACKGROUND OF THE TECHNOLOGY

According to the Environment Agency, as mass concentration measurement for general atmospheric fine particulate matter PM2.5 is affected by influences such as moisture and semi-volatile organic compounds, it is said that the measurement from the sample by a collection filter is difficult and unresolved.

EPA in the United State and European Union also standardize for measurement methods and present provisions for removing the differences of the data due to influence factors as much as possible.

Besides, also regarding the constituents of PM 2.5, component measurement manuals for ion component, carbon component, metal component and polycyclic aromatic hydrocarbon component are determined, but they have many parts to be developed and necessities to evaluate effectivity and availability of various measuring instruments or the like and to advance the establishment of the measuring methods are described.

Above all, in analyzation of the carbon component, a thermal separation method that has been popular cannot obtain satisfactory accuracy, though thermal separation/heat decomposition correction method is present as a powerful technique, because all analyzers are made by U.S. or European companies, it is described that the population of the analyzing method with the same level of accuracy and sensitivity by promoting the development domestically.

Currently, as PM2.5 flied from the other countries has become the major domestic environmental issues, measures such as installation of measuring instruments in each prefecture and city has become urgent.

A filtering method installed currently is to perform the measurement of mass concentration defined as a standard measuring method for PM2.5 in the United States and European Union. Since atmospheric fine particulate matter gives influence wielding to the atmosphere and enormous influence to the health by entering into the human lungs deeply, so that damage must be prevented by researching the components and derivation of evolution or the like as soon as possible.

Above all, the carbon component is a main component of floating dusts, since the analysis becomes important hint, organic carbon (OC) and elemental carbon (EC) are defined in the seven fractions and measuring conditions. As a measuring method, a heat manganese dioxide oxidation method and a heat separation optics revision method are applied generally, an analyzer that is applied widely on IMPROVE (Interagency Monitoring of Protected Visual Environment) in the United States detects methane reducing $CO_2$ by an FID detector made by DRI and SUNSET.

Calibration line uses 5% methane in helium and 5% carbon in $CO_2$, potassium hydrogen phthalate KHP and Sucrose standard solution for calibration injection. In the case of 5% methane in helium, calibration is performed by injecting volume of 100, 250, 1000, 1500 µL by 1000 µL and 2500 µL syringe. In order to minimize the influence of performance measurement in the FID or electrical drift, concentration calibration in the carbon Analyzer is extremely important.

Furthermore, in the thermal separation that is a mainstream for measurement of carbon component in present atmospheric fine particulate matter, OC (Organic Carbon) and EC (Elemental Carbon) are analyzed fractionally by being liberated from the measurement sample at different temperatures and at an oxidation atmosphere, based on supposition that organic material can be separated by volatilization at low temperature in He stream and that EC cannot be oxidized and separated at the same time, because there is necessity such that the correction for being detected as EC by thermally decomposing and carbonizing the organic material on the process of heating and separation is performed, the thermal separation optical correction method is used mainly. This method was developed in the above-mentioned DRI (Desert Research Institute) in the United State and is a method for correcting by change of reflectivity and transmission of a laser, measurement interference matters such that color in some kind of minerals in soil is changed by heating, that sublimation of the colored organic matters influences to correction by the laser light, that unevenness of the sample on the filter influences to reflection and transmission of light, that a large error in OC value is caused when a carbon fraction peak of the EC1 exceeds 50 µg, or the like, are pointed out.

On the other hand, in Japan, measurement of organic carbon and elemental carbon by an organic elemental analyzer is also attempted and a organic elemental analyzer has been used in research and each measurement institutions for PM2.5, but since this elemental analyzer doesn't have the function such as to accurately separate the organic carbon and inorganic carbon, OC is measured small, EC is measured excessively and detection at low concentration of OC and EC is impossible in this analyzer. Since PM2.5 brings big damage to the health, accurate measurement of PM2.5 is an urgent issue, and it is desired that the development of domestic instruments in order to be popularized widely.

DOCUMENT FOR PRIOR ART

Non-Patent Literature

1. Real face of the CHN coder Hozumi Keiichiro supervision Yanaco Analytical Industry Co., Ltd. Technology Group Edit 1993
2. Fine particulate matter in the air (PM2.5) component measurement manual Apr. 19, 2012 Ministry of the Environment

SUMMARY OF THE INVENTION

Problem to be Solved by the Invention

In the thermal separation, OC (organic carbon) and EC (elemental carbon) are defined by the analyzing method. The first problem is that definition of EC is different between the thermal manganese dioxide oxidation method and the thermal separation thermal decomposition correction method applied generally, the former of which is a carbon component that cannot be oxidized by manganese dioxide up to 525° C., the latter of which is a carbon component involving absorption of light by focusing on the nature that EC absorbs light, or the like, so that there is a problem such that the true value in each analyzing method does not conform.

The second problem is that, because standard substances for calibration of the detection use methane gas for correction (95% He+5% CH4), phthalic acid hydrogen potassium KHP and sucrose solution for each amount of composite injection, there is no way to evaluate the true value since the true value of carbon (μg) in detectable amounts depends on handling technology of measurement of each standard materials.

The third problem is that there is no validation to definition for terms of OC and EC and that differences between every carbon fractions are recognized, so that it would be not to be able to compare results by different protocols in the fraction level. As an example, the full amount of carbon is defined as OC1+OC2+OC3+OC4+EC1+EC2+EC3 and the value measured at the highest temperature from the start and the total amount of carbon fractions measured separately might not be matched, and further, carbonate carbon (CC) must be measured separately, the other total carbon in the environmental measurement does not match. Now in the measurement condition of the total carbon, there is a case that even organic compound is burned incompletely in the condition of oxygen 2% at 800° C., so that chemical resolution to the heat separation in the carbon component is insufficient.

The fourth problem is that: since DRI regarded as the best gas measurement needs four high pressure gases that are He, $O_2$, $H_2$ and compressed air and there are many kinds of controlled reagents such as reagents for calibration, oxidizing agents, reducing agents, hydrochloric acid, deionized distilled water and the like, the management for them and preparation of reagents are taken a lot of trouble, so that what is rapid and easy is required as an environmental measuring instrument.

Also in a mass concentration measurement method, due to moisture reservation in the filer catching PM2.5, in order to measure mass of fine particulate matters, the filter must be dried a few hours under certain conditions. Now, PM2.5 such as yellow dust flied from the neighbor countries has to be measured hourly, so that the fifth problem is a method for obtaining measured values rapidly and correctly to avoid the trouble of having to be dried under the certain conditions.

Means for Solving the Problems

The present invention for solving the above-mentioned problems is an analysis measurement system having a combustion tube installing samples for measuring carbon component in fine particulate matter, a combustion oven for heating the samples installed in the combustion tube and a calculation means for obtaining content of the carbon component (μg) from gases generated from the sample heated in the combustion oven, characterized by having a first oven for setting temperatures separating carbon fractions of OC, EC and CC and a second oven that oxidizing the carbon component to $CO_2$ by combustion, having a step for heating the combustion tube at each temperature defined to the carbon component fractions to separate and heat OC in said first oven, a step for heating the carbon component at a certain temperature from 550° C. to 1050° C. with addition of oxygen and metal catalysis filled in said combustion tube to oxidize the carbon component completely to $CO_2$, a step for adjusting the generated $CO_2$ to concentration suitable to be detected, and a TCD detector for detecting $CO_2$, and making a calibration line of relational expression to change of electrical resistance value corresponding to change of concentration of carbon dioxide gas due to organic compound standard samples in order to measure amount of carbon component (μg).

Furthermore, the present invention is An analysis measurement system having a combustion tube installing samples for measuring carbon component in fine particulate matter, a combustion oven for heating the samples installed in the combustion tube and a calculation means for obtaining content of the carbon component (μg) from gases generated from the sample heated in the combustion oven, characterized by having a first oven for setting temperatures separating carbon fractions of OC, EC and CC and a second oven that oxidizing the carbon component to $CO_2$ by combustion, having a step for heating the combustion tube at each temperature defined to the carbon component fractions to separate and heat OC in said first oven, a step for heating the carbon component at a certain temperature from 550° C. to 1050° C. with addition of oxygen and metal catalysis filled in said combustion tube to oxidize the carbon component completely to $CO_2$, a step for adjusting the generated moisture and $CO_2$ to concentration suitable to be detected, and two TCD detectors for detecting moisture and $CO_2$ respectively, and making a calibration line of relational expression to change of electrical resistance value corresponding to change of concentration of moisture and carbon dioxide gas generated on every process in the first and the second ovens due to organic compound standard samples in order to measure moisture content (μg) and amount of carbon component (μg).

Moreover, the present invention is characterized by, in the above mentioned analysis measurement system, having a third oven installing a reducing tube filled with reduced copper and heating it at 550° C. and a TCD detector for nitrogen, reducing nitrogen dioxide from the first and the second ovens in the third oven to make nitrogen gas, and making a calibration line of relational expression to change of electrical resistance value corresponding to change of concentration of the nitrogen gas detected by the TCD detector due to organic compound standard samples in order to measure amount of nitrogen together with moisture content (μg) and amount of carbon component (μg) generated on every process in the first and the second ovens.

Effect of the Invention

Firstly, the method of the present invention has an effect that correction by carbonization is not necessary because original OC and EC can be measured separately by complete combustion by grasping matters generated by incomplete combustion/oxidation respectively carried out in processes of C1 to C4, namely mattes by carbonization, per each carbon fractions, for complex changes in elemental carbon generated by thermal decomposition of organic carbon in a process of thermal decomposition of carbon component in the fine particulate matter in the air.

Secondly, since separation due to the measurement conditions defined in the carbon fractions is detected as accurate amount of carbon, there is an effect that consistency to the whole carbon is measured as a total value of OC, EC and CC.

Thirdly, there is an effect such as to make validation of each amount of carbon (μg) in carbon fractions to an international standard if organic standard samples authenticated in an international unit SI system are used since the amount of carbon in each carbon fractions can be established simply by a calibration line system based on mass of an organic compound standard sample and the calibration system can be evaluated by using different organic compounds.

Fourthly, OC/EC ratio important to calculation of the occurrence of PM2.5 can be measured more accurately as OC and EC are obtained from the same calibration line.

Fifthly, there is an effect that correction for moisture content can be calculated easily from mass of a filter catching PM2.5 since the analysis system of the present invention can detect the accuracy content of moisture (μg) at the same time.

Sixthly, if the third oven for heating the reducing tube filled with a reducing agent at 550° C. is installed, since measurement of nitrogen and nitrogen oxide can be carried out, the measurement can contribute to component analysis as reference data.

Lastly, as the most important effect, a principle of an organic element analyzer Yanaco CHN coder is to catch gas connected to oxygen by combusting samples to sodium hydroxide of an absorption agent based on chemical reaction explained in so called law of conservation of mass, to take changes of detected gas concentration before and after the result as difference of specific heat conductivity, to measure detectable amount (μg) due to a correlating equation to content figured from content rate of organic compound, and to have a system to be able to evaluate the detectable amount due to the other organic compound different in the content rate.

In general, though a method of measurement using a calibration line depends on the confidence in the calibration line in itself, the measurement system of the organic element analyzer is provided with an advantageous characteristic that can be evaluated with composition ratio of the other organic compounds, and traceability of mass is established until a used 1 mg weight of the balance for standard sample weights, so that it is the most reliable method for comparing the true value between every measurement place or internationally.

The mass data of the balance and the electrical signals of the analyzer are printed out automatically, if considering calculation process of calculation software, also the data processing is a system establishing clear believability, so that it is considered to have an important role in PM2.5 measurement on a global scale together with establishment in an international standard of elemental analysis standard samples.

MODE FOR CARRYING OUT THE INVENTION

Figure 1:
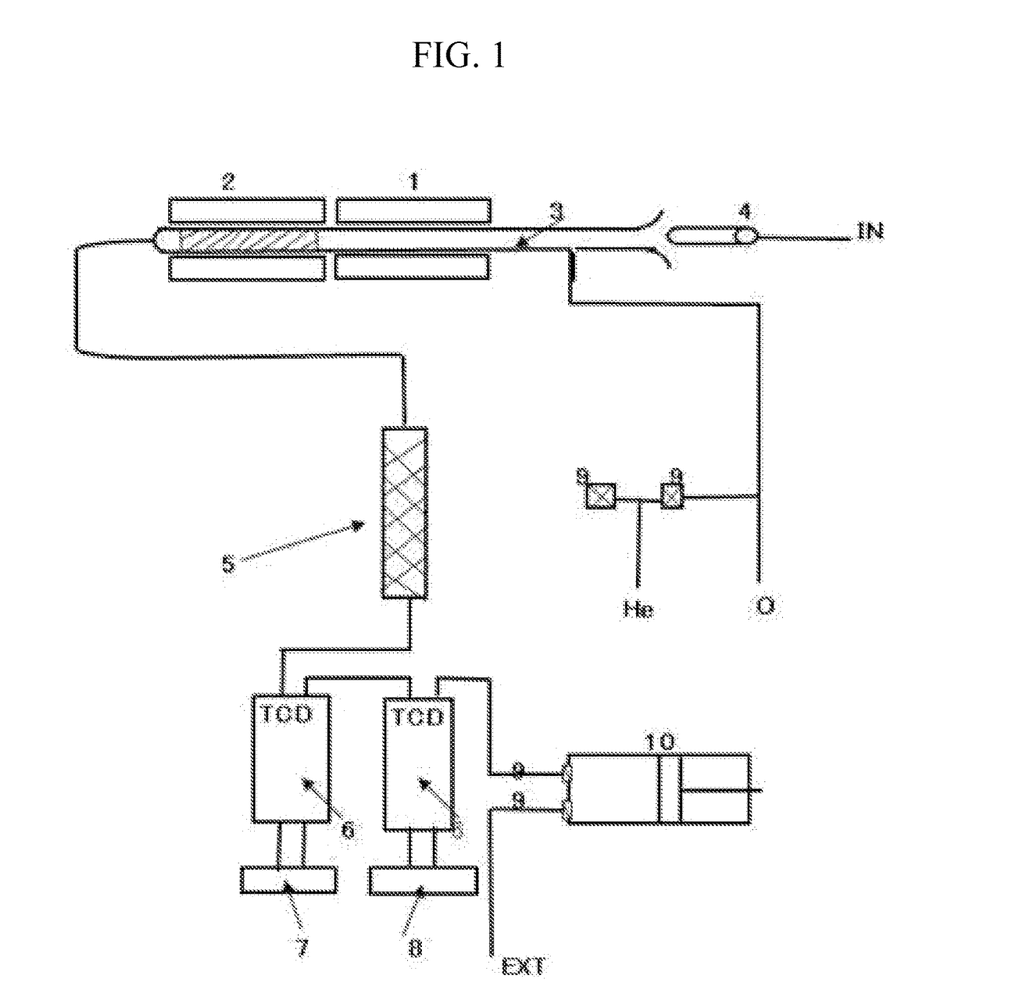
FIG. 1 is a system constitution in an analysis device of the present invention.

As shown in FIG. 1, a system constitution of an analysis device according to a working mode of the present invention is to have combustion tube crossing two ovens or combustion tubes installing on two ovens respectively, wherein a first oven is used for separating carbon fractions and a second oven combusts every carbon fraction completely with enough oxygen, an effect of metal catalyst filled in the combustion tube and high temperature in order to carry out accuracy detection. There is a diffuser before going to a detection system to make the measured gas to proper detection concentration.

Firstly, change of electrical signals before and after passing through a moisture absorption tube is measured by a detector, and H (μg) is determined due to a calibration line obtained with organic compound standard samples in advance.

Next, change of electrical signals before and after passing through an absorption tube for carbon dioxide gas is measured by a detector, and C (μg) is determined due to a calibration line obtained with organic compound standard samples in advance similarly. A suction pump is installed at an end thereof as a constant speed device.

Working Example No. 1

Figure 2:
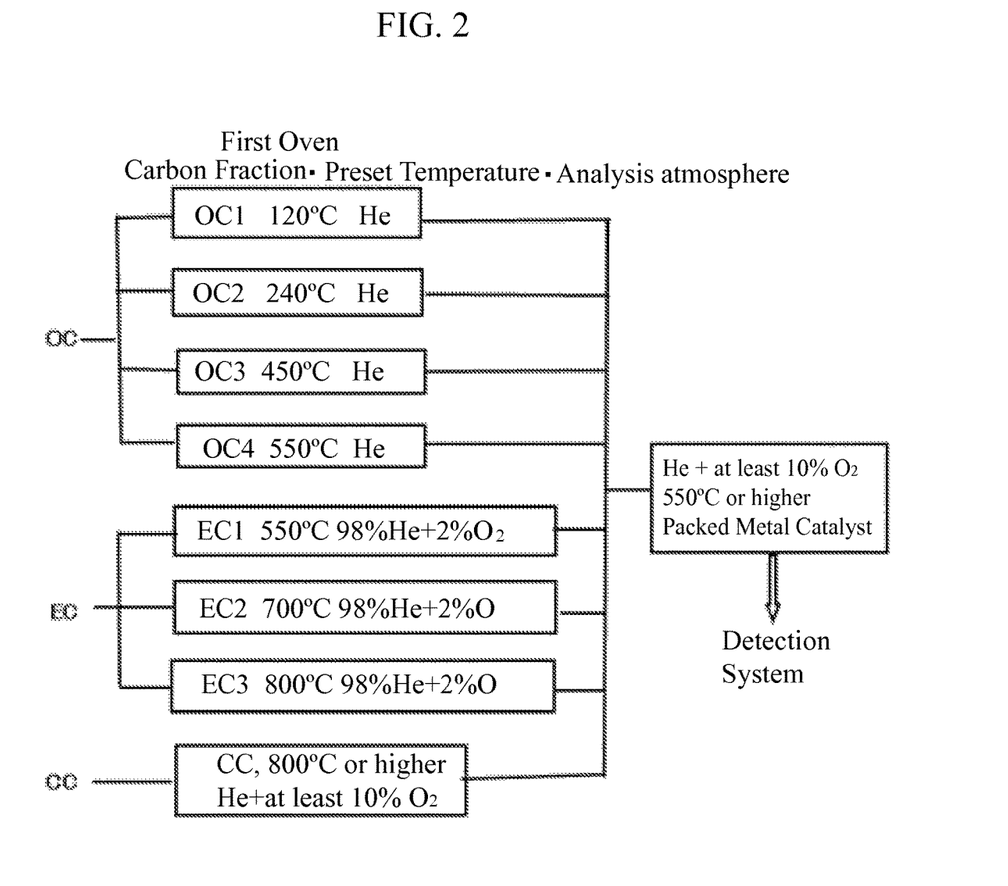
FIG. 2 is a constitution of the carbon fractions and the measurement conditions of the present invention.

As shown in FIG. 2, setting temperatures of the carbon fractions and analysis atmosphere are determined and separated in the first oven, and the carbon components are made to carbon dioxide gas by enough oxygen amount, metal catalyst and high temperature combustion in the second oven. Every carbon fraction is determined in the same calibration line in the second oven and the total amount of moisture in the measured value is used for correcting weight of the sample. The total value of every carbon fraction matches the total amount of carbon measured in the case that the sample enters directly into the second oven. Even if the carbon fractions are omitted, organic carbon and inorganic carbon can be measured accurately by measurement of OC, EC and CC.

Figure 3A:
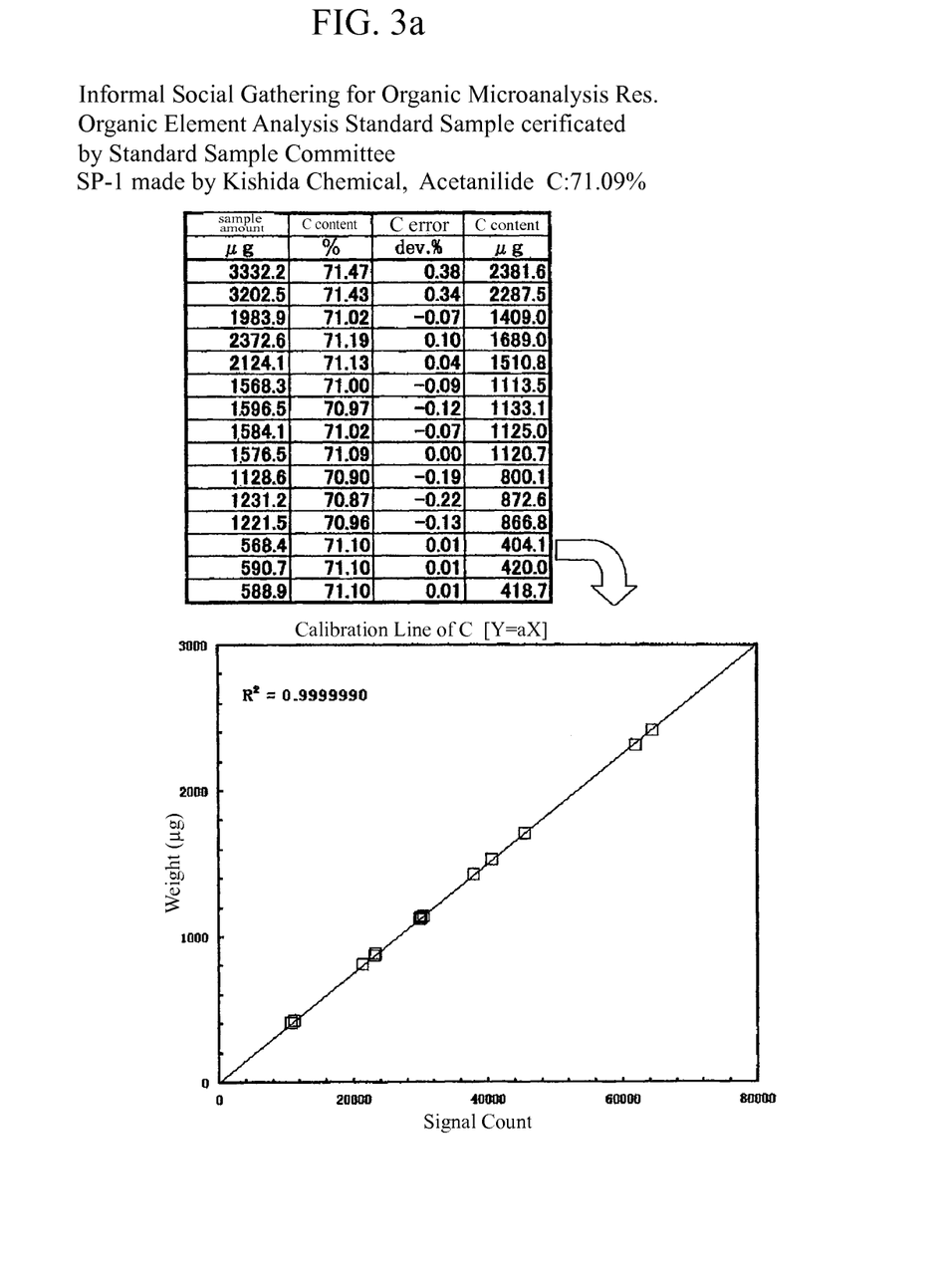
FIG. 3 is a diagram showing the calibration line in TCD detector in the analysis device according to the present invention.

As shown in FIG. 3a, the calibration line was made by using authenticated organic compound standard sample. In this working example, the existing elemental analyzer (Yanaco CHN corder MT-6) was used and an elemental analysis standard sample SP-1 made by Kishida Chemical certificated by Standard Sample Committee of Informal Social Gathering for Organic Microanalysis Res. was used, but, if using the standard sample certified internationally, this analysis system is useful as an international standard device.

Figure 3B:
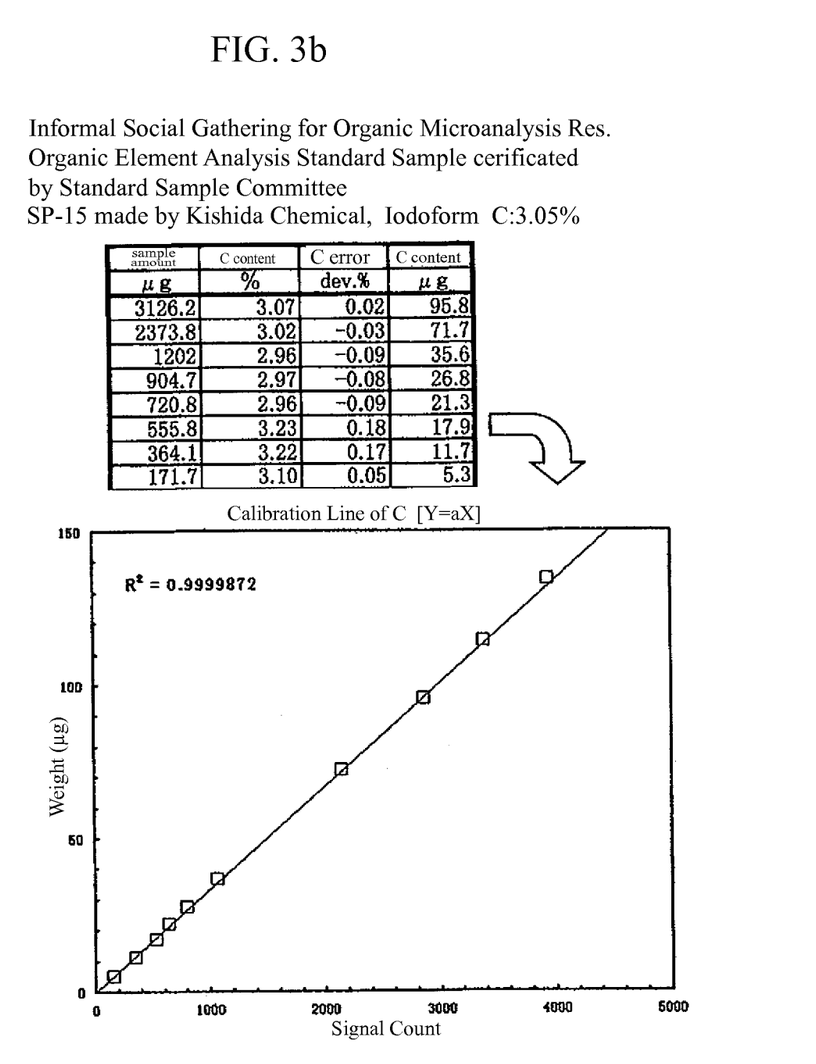

Though a measuring method for international standard has not been established yet, a guideline for an air quality by WHO is 25 ($\mu g/m^3$) of a daily average and extremely low value of the carbon component thereof must be measured, but, in a working example shown in FIG. 3b, an elemental analysis standard sample SP-15 made by Kishida Chemical certificated by Standard Sample Committee of Informal Social Gathering for Organic Microanalysis Res. was used similarly, and 5.3 μg of carbon was detected, and further, if the diffuser in the method according to the present invention makes low concentration impossible to be measured in existing devices proper, it can achieve detection capability close to FID detector.

Figure 4:
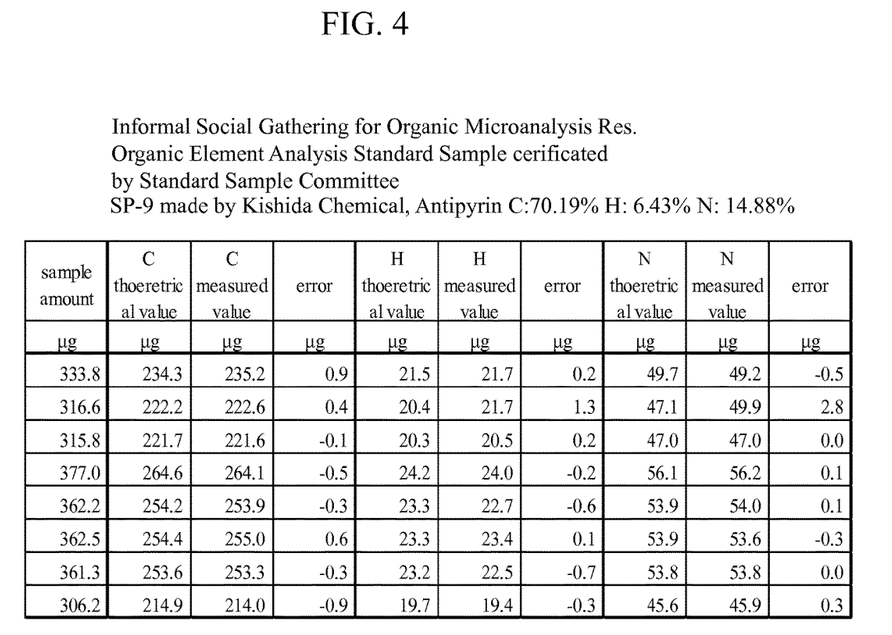
FIG. 4 is a diagram showing detected samples at low concentration in TCD detector in the analysis device according to the present invention.

The working mode shown in FIG. 4 shows analysis errors verified by using an elemental analysis standard sample SP-9 made by Kishida Chemical certificated by Standard Sample Committee of Informal Social Gathering for Organic Microanalysis Res. by the existing elemental analyzer (Yanaco CHN corder MT-6), the analysis errors are 0.1-0.9 μg and 0.1-1.3 μg about carbon amount and hydrogen amount (μg) respectively. Though this detection is analytical precision about the concentration in the case of attenuating combustion gas with He by 150 mL of the pump, the analysis device according to the present invention uses as a constant speed function by placing the pump for attenuating the combustion gas at the rear of the detector, and the diffuser is installed at the position instead of the pump to make homogeneous but not to attenuate, so that detection in the low concentration can be possible by ability of FID detector.

Figure 5:
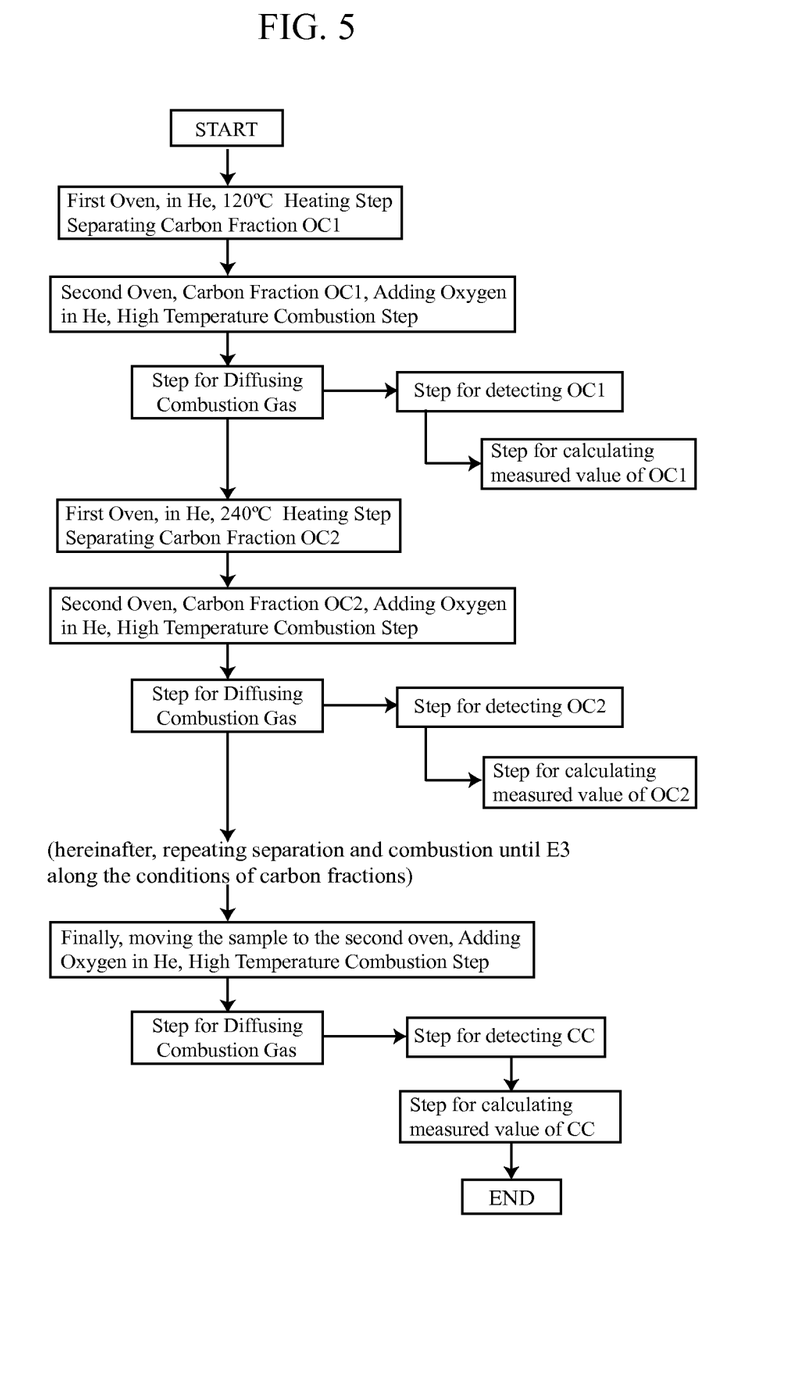
FIG. 5 is a flow chart of fractional determination of carbon fractions of the present invention.
Figure 6:
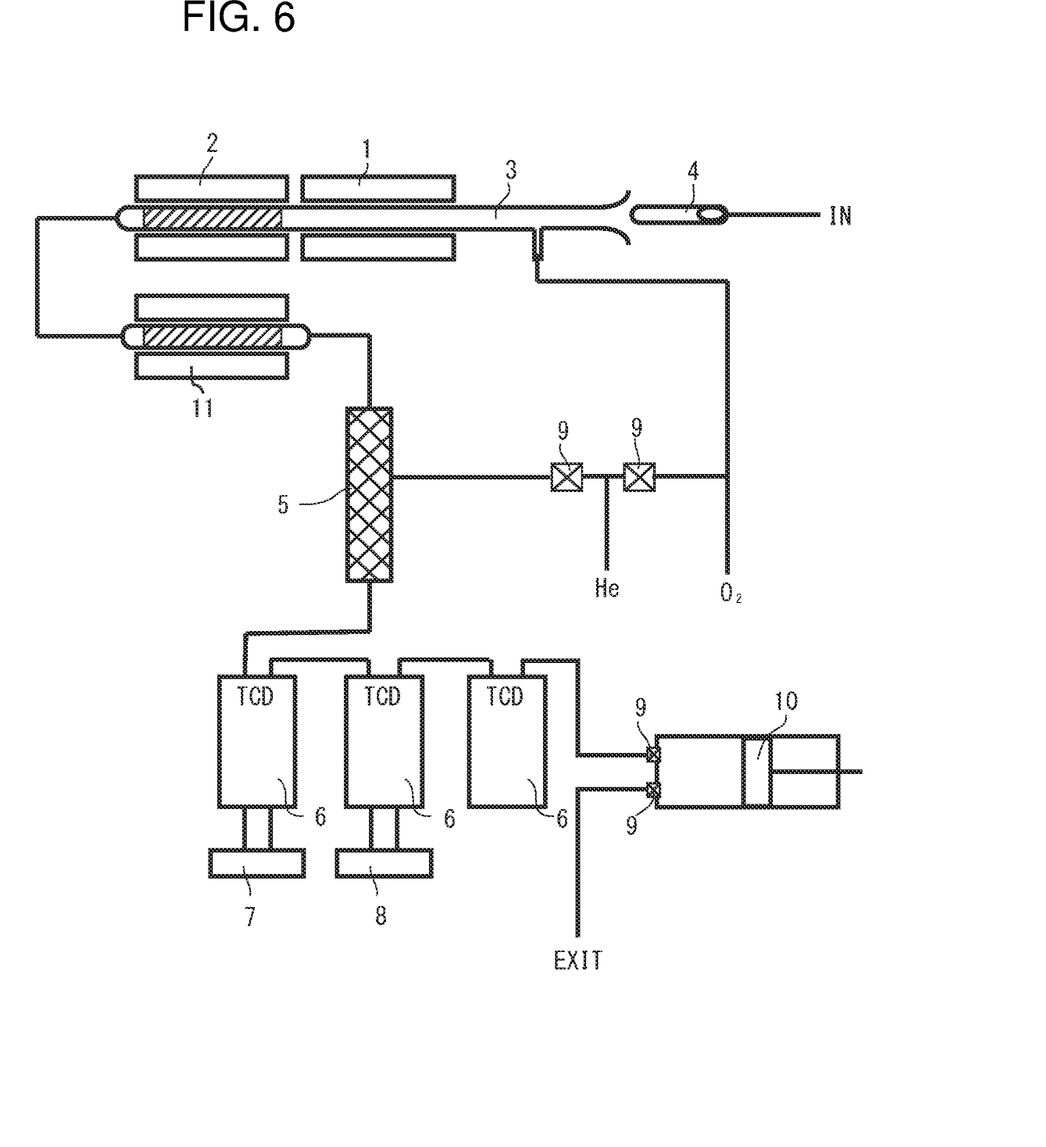
FIG. 6 is another embodiment of a system constitution in an analysis device of the present invention.
Figure 7:
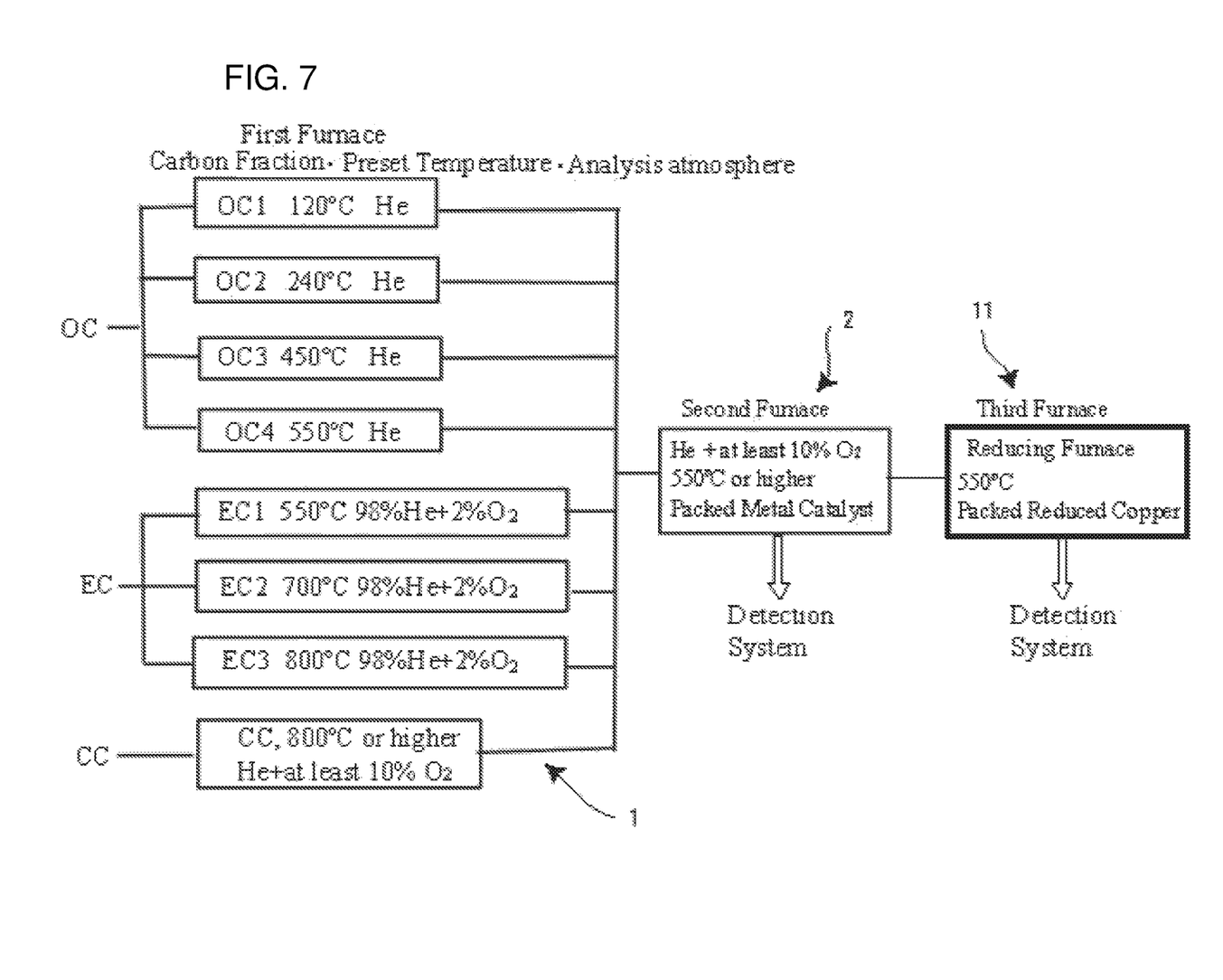
FIG. 7 is another embodiment of a constitution of the carbon fractions and the measurement conditions of the other embodiment.

FIG. 5 shows a flowchart of this working mode. If PM2.5 trapped on the quartz filter enters into the first oven together with the quartz filter, working advances along a program based on the flowchart automatically to obtain C (μg) and H (μg). Firstly, OC1 is separated at a heating step, and next, oxygen is added enough to be combusted OC1 completely at a high temperature step, and then, OC1 is adjusted to suitable detection concentration at a diffusion step, and finally, by advancing to a detection step, measured value of OC1 can be obtained in a measurement value calculation step.

Subsequently, in the heating step, OC2 is separated, and the working is repeated to the measurement value calculation step. The calibration line is simple because using the same line in every carbon fraction. If N detector is added therein, N can be measured at the same time. If the mass concentration is corrected by obtaining the moisture content from the total amount of hydrogen and mass concentration of PM2.5, there is an advantage to be able to obtain the mass concentration without the trouble for drying accurately.

INDUSTRIAL APPLICABILITY

Environmental problem by PM2.5 is not only domestic, and a lot of PM2.5 flied from neighbor countries is serious in our country and in human health. Though it involves business activity in agriculture or in industry deeply, there is also possibility that analysis of atmosphere dust by the measurement causes new industry. The method that can measure easily according to the invention is useful in the foreign countries as an independent technology and can be disseminated widely.

The method according to the present invention is effective as a means for measurement along the international standard because reliability of the measured value can be proved if reliability of the measured value is measured together with data of the standard samples traced in the suitable different international System of Units SI as a monitor corresponding to the detected amount near the measured value of the sample by using the calibration line using the standard sample traced in the International System of Units SI.

EXPLAIN OF LETTERS OR NUMERALS

1. The first oven for separation of carbon fractions
2. The second oven for combustion of carbon fractions
3. Combustion tube
4. Sample introduction bar
5. Combustion gas diffuser
6. TCD detector
7. $H_2O$ absorption tube
8. $CO^2$ absorption tube
9. Magnetic valve
10. Constant-speed suction pump
11. Third furnace (reduction furnace)

The invention claimed is:

1. An analysis measurement method, in a combustion type analysis measurement system for measuring a carbon component of a fine particulate matter comprising a first furnace, a second furnace, a combustion tube arranged over the first furnace and the second furnace and having a metal catalyst filled in a portion corresponding to the second furnace, and a TCD detector, the method comprising:
    a step a) for thermally separating organic carbon by heating a sample including the fine particulate matter in the combustion tube to a temperature from 120° C. to 550° C. corresponding to an organic carbon fraction, and thermally separating elemental carbon by heating the sample to a temperature not less than 550° C. corresponding to an elemental carbon fraction while adding oxygen in the first furnace,
    a step b) for adding oxygen to the sample and heating the metal catalyst filled in the combustion tube in which the sample and oxygen pass through at a temperature from 550° C. to 1050° C. to oxidize the carbon component completely to $CO_2$ in the second furnace, and
    a step c) for measuring $CO_2$ produced by completely oxidizing a low carbon-containing organic compound standard sample whose carbon content is known by heating in the first furnace and oxidizing in the second furnace as in steps a) and b), making a calibration line that is a relational expression between an electric signal output from the TCD detector and the carbon content of the low carbon-containing organic compound standard sample, and measuring an amount of the carbon component of the fine particulate matter with the TCD detector based on the calibration line.

2. A combustion type analysis measurement system for measuring a carbon component of a fine particulate matter, comprising:
    a combustion tube arranged over a first furnace and a second furnace and having a metal catalyst filled in a portion corresponding to the second furnace,
    a first furnace for thermally separating organic carbon by heating a sample including a fine particulate matter in the combustion tube to a temperature from 120° C. to 550° C. corresponding to an organic carbon fraction, and thermally separating an elemental carbon by heating the sample to a temperature not less than 550° C. corresponding to an elemental carbon fraction while adding oxygen, and
    a second furnace for adding oxygen to the sample and heating a metal catalyst filled in said combustion tube in which the sample and oxygen pass through at a temperature from 550° C. to 1050° C. to oxidize the carbon component completely to $CO_2$, and
    a TCD detector for measuring an amount of the carbon component of the fine particulate matter by first measuring $CO_2$ produced by completely oxidizing a low carbon-containing organic compound standard sample whose carbon content is known by heating in the first furnace and oxidizing in the second furnace, making a calibration line that is a relational expression between an electric signal output from the TCD detector and the carbon content of the low carbon-containing organic compound standard sample, and measuring the amount of the carbon component of the fine particulate matter with the TCD detector based on the calibration line.

3. The combustion type analysis measurement system according to claim 2, further comprising a TCD detector for measuring moisture of the sample by first measuring moisture produced by making a low moisture-containing organic compound standard sample whose moisture content is known by heating in the first furnace and oxidizing in the second furnace, making a calibration line that is a relational expression between an electric signal output from the TCD detector for measuring moisture of the sample and the moisture content of the low moisture-containing organic compound standard sample, and measuring the amount of moisture of the fine particulate matter with TCD detector for measuring moisture of the sample based on the calibration line.

* * * * *